United States Patent [19]
Laine et al.

[11] Patent Number: 5,693,519
[45] Date of Patent: Dec. 2, 1997

[54] THERMOSTABLE, SALT TOLERANT, WIDE PH RANGE NOVEL CHITOBIASE

[75] Inventors: Roger A. Laine, Baton Rouge, La.; Chin-Yih Ou, Dunwoody, Ga.

[73] Assignee: Board of Supervisors of Louisiana State University and Agricultural and Mechanical College, Baton Rouge, La.

[21] Appl. No.: 455,837

[22] Filed: May 31, 1995

Related U.S. Application Data

[62] Division of Ser. No. 171,208, Dec. 21, 1993, Pat. No. 5,602,020, which is a continuation of Ser. No. 844,301, Feb. 27, 1992, abandoned.

[51] Int. Cl.$^6$ .................. C12N 15/56; C12N 15/70; C12N 1/21; C12N 9/42
[52] U.S. Cl. .................. 435/209; 435/200; 435/172.3; 435/252.3; 435/252.33; 435/320.1; 536/23.1; 536/23.2
[58] Field of Search .................. 536/23.1, 23.2; 435/200, 209, 172.3, 252.3, 252.33, 320.1

[56] References Cited

PUBLICATIONS

Jannatipour et al., "Translocation of *vibrio harveyi* N, N'—Diacetylchitobiase to the Outer Membrane of *Escherichia coli*," J. Bacteriol. vol. 169, pp. 3785–3791 (1987).
Soto–Gil et al;., "N, N'—Diacetylchitobiase of *Vibrio harveyi*," J. Biol. Chem. vol. 264, No. 25, pp. 14,778–783 (1989).
Wortman et al., "Chitinase Determinants of *Vibrio vulnificus*: Gene Cloning and Applications of a Chitinase Probe," Appl. Environ. Microbiol., vol. 52, No. 1, pp. 142–145 (1986).
Kless et al., "Cloning of the Gene Coding for Chitobiase of *Serratia marcescens*," Mol. Gen. Genet., vol. 217, pp. 471–473 (1989).
Facsimile letter from roger Laine to Scott Davis (Feb. 13, 1991).
Zhu et al., "Chitobiase/B–N–Acetylhexosaminidase from *Vibrio Parahemolyticus*: Salt Tolerant and Wide pH Range of Activity—Isolation, Characterization and Molecular Cloning," FASEB J., 5(6) A1507 Abstract #6589 (Apr. 1991).
B.C.R. Zhu et al. "Chitobiase/B–N–Acetylhexosaminidase From Vibrio Parahemolyticus: Salt Tolerant and Wide pH Range of Activity—Isolation, Characterization and Molecular Cloning", FASEB J.5(6) A1507, Abst. #6589 1991.

*Primary Examiner*—Rebecca E. Prouty
*Attorney, Agent, or Firm*—John H. Runnels

[57] ABSTRACT

A cloned chitobiase from a *Vibrio parahemolyticus* gene cloned into the plasmid pUC18 in *E. coli* strain DH5α. The plasmid construct, called pC120, had a 6.4 kb DNA insert. The recombinant gene expressed chitobiase activity similar to that found in native *V. parahemolyticus*. In addition to chitobiose, at least six additional substrates were observed to be hydrolyzed by the recombinant chitobiase, including β-N-acetyl galactosamine glycosides, showing that the enzyme is an N-acetyl-hexosaminidase. The enzyme showed resistance to denaturation by 2M NaCl, was thermostable at 45° C., and possessed an unusual range of activity from pH 5 to 9. The enzyme is useful in the degradation of crustacean shells. It catalyzes the production of N-acetyl-glucosamine, a compound which should be valuable as a chiral precursor or intermediate in the synthesis or manufacture of pharmaceutical compounds.

18 Claims, 1 Drawing Sheet

| Substrate | Activity | Relative rates (%) | Assay |
|---|---|---|---|
| p-nitrophenyl-β-N-acetylglucosamine | +++ | 100 | O.D. 420 |
| p-nitrophenyl-β-N-acetylgalactosamine | + | 18 | O.D. 420 |
| p-nitrophenyl-β-NN'-diacetylchitobiose | ++ | 66 | O.D. 420 |
| β-GlcNAc-(1-3)-β-Gal-(1-4)GlcNAc | + | not determined | HPLC |
| Diacetylchitobiose | +++ | not determined | HPLC |
| Triacetylchitotriose | ++ | not determined | HPLC |
| Tetraacetylchitotetraose | ++ | not determined | HPLC |
| p-nitrophenyl-α-N-acetylglucosamine | - | | O.D. 420 |
| p-nitrophenyl-α-N-acetylgalactosamine | - | | O.D. 420 |
| p-nitrophenyl-β-N-acetyl-1-thioglucosamine | - | | O.D. 420 |
| p-nitrophenyl-β-N-acetyl-6-sulfate-glucosamine | - | | O.D. 420 |
| p-nitrophenyl-α-glucopyranoside | - | | O.D. 420 |
| p-nitrophenyl-β-glucopyranoside | - | | O.D. 420 |
| p-nitrophenyl-α-galactopyranoside | - | | O.D. 420 |
| p-nitrophenyl-β-galactopyranoside | - | | O.D. 420 |
| p-nitrophenyl-α-mannopyranoside | - | | O.D. 420 |
| p-nitrophenyl-β-mannopyranoside | - | | O.D. 420 |
| Globoside | - | | TLC |
| GM2 | - | | TLC |
| Asialo-GM2 | - | | TLC |

THERMOSTABLE, SALT TOLERANT, WIDE PH RANGE NOVEL CHITOBIASE

This is a divisional of application Ser. No. 08/171,208 now U.S. Pat. No. 5,602,020, filed Dec. 21, 1993, which is a continuation of application Ser. No. 07/844,301, filed Feb. 27, 1992, now abandoned, the entire disclosure of which is incorporated by reference.

The development of this invention was partially funded by the Government under grant NA85AA-D-SG141 from the National Oceanic and Atmospheric Administration National Sea Grant College Program. The Government may have certain rights in this invention.

This invention pertains to chitobiases, particularly to a novel purified chitobiase cloned from *Vibrio parahemolyticus*.

Chitin is one of the largest sources of renewable biomass on earth, second only to cellulose and lignins. Chitin is a class of polymers of N-acetyl-glucosamine. It is a major cell wall component of many agronomically important pests, including most fungi. Chitin is also a major component of the cuticles of crustaceans and insects. Chitin may be broken into disaccharides or other low molecular weight multimers by a chitinase, and then to 2-deoxy-2-acetamido-D-glucose (also called N-acetyl-glucosamine) by a chitobiase. The term "chitinase" generally describes an enzyme that specifically hydrolyzes a chitin to one or more chitooligomers (See EC 3.2.2.14). The term "chitobiase" generally describes an enzyme that specifically hydrolyzes one or more chitooligomers such as diacetylchitobiose, particularly hydrolyzing such compounds to N-acetyl-glucosamine or other N-acetyl-hexosamines (See EC 3.2.1.30). Many different types of chitobiases occur naturally. For example, chitobiases are found in microbes such as Serratia, Vibrio, and Streptomyces. No commercial chitobiase purified from a molecularly cloned gene has previously been available.

The end product of hydrolysis of chitin, first by a chitinase, and then by a chitobiase, is typically 2-deoxy-2-acetamido-D-glucose, which is a chiral compound. This chiral compound should be valuable as a chiral precursor or intermediate in the synthesis of chiral pharmaceutical compounds, such as TnTs sialyl, TnTs sialyl tumor surface antigen, sialyl Le$^x$, and lymphocyte hormone receptor. In addition, a chitobiase is useful as a reagent in the degradation of crustacean shells or other chitin-containing waste, to reduce waste disposal problems or to manufacturer fertilizer.

Jannatipour et al., "Translocation of *Vibrio harveyi* N,N'-Diacetylchitobiase to the Outer Membrane of *Escherichia coli*," J. Bacteriol., vol. 169, pp. 3785–3791 (1987); and Soto-Gil et al., "N,N'-Diacetylchitobiase of *Vibrio harveyi*," J. Biol. Chem. vol. 264, No. 25, pp. 14,778–14,783 (1989) disclose the cloning and sequencing of a chitobiase gene from the species *Vibrio harveyi*. No information is given on the thermostability, salt tolerance, or pH range of this chitobiase. The *V. harveyi* chitobiase is transported to the outer membrane of *E. coli* when expressed in that bacterium.

Wortman et al., "Chitinase Determinants of *Vibrio vulnificus*: Gene Cloning and Applications of a Chitinase Probe," Appl. Environ. Microbiol., Vol. 52, No. 1, pp. 142–145 (1986) discloses the cloning of a chitobiase gene from the species *Vibrio vulnificus*. No information is given on the thermostability, salt tolerance, or pH range of this chitobiase.

Kless et al., "Cloning of the Gene Coding for Chitobiase of *Serratia marcescens*," Mol. Gen. Genet., vol. 217, pp. 471–473 (1989) discloses the cloning of a chitobiase gene from the species *Serratia marcescens*. No information is given on the thermostability, salt tolerance, or pH range of this chitobiase.

BRIEF DESCRIPTION OF THE DRAWING

The figure depicts a table giving substrate specificities of the cloned chitobiase.

A novel chitobiase, Chitobiase VP2, has been produced by cloning the chitobiase gene from *Vibrio parahemolyticus* into *E. coli*, where the gene has subsequently been expressed. This novel chitobiase has been purified, and has shown unusual physical characteristics: The enzyme was salt tolerant, retaining 85% of its activity in a pH 7.0 buffer in the presence of 1M NaCl, 56 % of its activity at 2M NaCl, and 28 % at 3M NaCl. The unusual pH range of activity spanned acidic to basic conditions, from pH 5 to 9. The enzyme was thermostable at 40°–45° C. A search for homologues to its N-terminal amino acid partial sequence indicates that it is a novel protein. The salt tolerance, thermostability, and wide pH range of Chitobiase VF2 suggest that this novel and robust chitobiase will be useful in the industrial processing of chitin.

MATERIALS AND METHODS

Materials: Restriction endonucleases, T4 ligase, in vitro packaging reagents, and competent *E. coli* DH5α cells were purchased from Bethesda Research Laboratories (BRL). Alpha dCTP was purchased from ICN Biochemicals Inc. (Cleveland, Ohio). The various p-nitrophenyl derivatives and N-acetylamino sugars were purchased from Sigma Chemical Company (St. Louis, Mo.). Globoside, GM$_2$ and asialo-GM$_2$ were gifts from Dr. Y. T. Li and Dr. S. L. Li (Tulane Medical School, New Orleans, La.), and β-GlcNAc-(1–3)-βGal-(1–4)-GlcNAc was a gift from Drs. Saeed A. Abbas and Khushi L. Malta (Roswell Park Memorial Hospital, New York). The gas-phase determination of the chitobiase protein N-terminal sequence was performed at the Protein Chemistry Facility, Baylor College of Medicine, Houston, Tex.

Bacterial strains and plasmids: *Vibrio parahemolyticus* was obtained from the American Type Culture Collection (Rockville, Md.) (ATCC strain//27969) and the *E. coli* DH5α strain used as the bacterial host for recombinant plasmids was obtained from BRL. The *E. coli* strain DH5α was grown in a LB (Luria-Bertani) medium supplemented with ampicillin (50 μg/ml). The pUC18 plasmid was obtained from BRL.

Construction and screening of a *Vibrio parahemolyticus* plasmid DNA library for chitobiase expression: The chromosomal DNA of *Vibrio parahemolyticus* was partially digested with Sau3A restriction endonuclease, and fractionated in a 10–40% sucrose gradient. DNA fragments of 5–8 kbp and 7–12 kbp were introduced into the BamH-I sites of pUC18 plasmid. The recombinant pUC18 DNA was then used to transform competent *E. coli* DH5α cells. To screen for chitobiase activity, bacterial colonies with Vibrio-pUC18 DNA were stabbed into agar plates containing p-nitrophenyl-β-N-acetyl glucosamine (pNP-β-GlcNAc) in LB medium, and were incubated at 37° C. for 24 hours. Clones producing a bright yellow color indicated cleavage of the p-nitrophenyl-β-N-acetylglucosamine, and expressed presumptive chitobiase activity. Plasmid DNA isolated from these clones was then used to transform new *E. coli* DH5α cells, in order to amplify the plasmid. The resulting plasmid was called pC120, and the chitobiase was called Chitobiase VP2. This clone was grown on plates overlain with colloidal chitin, but it did not produce a clear zone on the plates, suggesting that the pC120 clone does not encode a functional, secreted chitinase.

A sample of this transformed *E. coli* strain DH5α with the cloned Chitobiase VP2 gene in plasmid pC120 was deposited with the American Type Culture Collection (ATCC), 12301 Parklawn Drive, Rockville, Md. 20852 on Feb. 26, 1992, and was assigned ATCC Accession No. 68920. This deposit was made pursuant to a contract between ATCC and the assignee of this patent application, Board of Supervisors of Louisiana State University and Agricultural and Mechanical College. The contract with ATCC provides for permanent availability of the progeny of this *E. coli* strain to the public on the issuance of the U.S. patent describing and identifying the deposit or the publication or the laying open to the public of any U.S. or foreign patent application, whichever comes first, and for availability of the progeny of this *E. coli* strain to one determined by the U.S. Commissioner of Patents and Trademarks to be entitled thereto according to 35 U.S.C. § 122 and the Commissioner's rules pursuant thereto (including 37 C.F.R. §1.14, with particular reference to 886 OG 638). The assignee of the present application has agreed that if the *E. coli* strain on deposit should die or be lost or destroyed when cultivated under suitable conditions, it will be promptly replaced on notification with a viable culture of the same *E. coli* strain.

Chitobiase activity assay: The assay system for chitobiase contained the following in 0.5 ml of solution: 50 mM phosphate buffer pH 7.0, 50 µl of 5 mM p-nitrophenyl-β-N-acetylglucosamine, and 1 µl to 100 µl of the enzyme solutions. The assay solutions were incubated for 30 min at 37° C., 2 ml of 1M $Na_2CO_3$ was then added to stop the reaction, and the $A_{420}$ (absorption at 420 nm) was read against a blank which contained buffer and p-nitrophenyl-β-N-acetylglucosamine. One unit of enzyme activity is defined as that which catalyses the formation of 1 µmol p-nitrophenol per minute; specific enzyme activity is expressed as unit/mg of protein.

Purification of chitobiase

Preparation of lysozyme extracts: A batch of 500 ml of *E. coli* carrying the pC120 plasmid was grown in LB supplemented with 50 µg/ml of ampicillin at 37° C. for 18 hrs. The medium was centrifuged at 600×g for 10 min. The cell pellet was suspended in 20 ml of 50 mM Tris-HCl buffer (pH 7.5) containing 15% sucrose, 10 mM EDTA, 20 mg lysozyme, 1 mM phenylmethane sulfonyl fluoride (PMSF), and was stirred at 4° C. for 30 min., followed by the addition of 20 ml of Triton X 100 solution (10% Triton X 100, 50 mM Tris-HCl pH 7.5, 10 mM EDTA), and 1 mM PMSF, and stirred at 4° C. overnight. The cell extracts were centrifuged at 25,000×g for 60 min. to remove chromosomal DNA. The supernatant was precipitated with ammonium sulphate. The material precipitating between 30%–60% saturation was collected by centrifugation, and dialysed against 10 mM sodium phosphate buffer pH 6.0. Protein was assayed by Bio-Rad protein assay reagent (Cambridge, Mass.) using bovine serum albumin as a standard.

DEAE-Biogel A Column chromatography, a type of anion exchange chromatography, was performed on a 2.5×25 cm column in 10 mM sodium phosphate buffer, pH 6.0. A 50 ml sample was applied to the column (equivalent to 500 ml of the original culture), and washed with the same buffer (20×bed volume). The enzyme was eluted with the same buffer containing a 0.1M to 0.3M linear gradient of NaCl.

Hydroxylapatite column chromatography:. The enzymatically active pool from the DEAE-Biogel A column was dialyzed against 10 mM phosphate buffer (pH 7.0) and applied onto a hydroxylapatite column (2×10 cm). Chitobiase was obtained by eluting with a linear gradient of 0 to 0.3M phosphate buffer.

Sephadex G-200 gel permeation column chromatography: After concentration with an Amicon pressure cell (Beverly, Mass.) equipped with a PM 10 filter (10,000 MW cutoff), the sample was chromatographed on a Sephadex G-200 column (2.0×100 cm) (Sigma Chemical, St. Louis, Mo.) equilibrated in 10 mM phosphate buffer (pH 7.0).

Fractionation

Fractionation of *E. coli* cells into extracellular, periplasmic and cytoplasmic fractions: Separation of *E. coli* cells into extracellular, periplasmic and cytoplasmic fractions was based on the procedure of Nossat and Heppel, J. Biol. Chem., Vol. 241, pp. 3055–3062 (1966), which is incorporated by reference. *E. coli* cells containing pC120 were grown in 50 ml of LB medium at 37° C. for 18 hours. Cells were concentrated by centrifugation, and all further steps were performed at 4° C. The culture supernatant was saved as the "extracellular fraction." The pellet was washed twice with 10 mM Tris-HCl (pH 7.3) containing 30 mM NaCl, and was then treated with pH 7.3 Tris-HCl buffer containing 1 mM EDTA and 20% sucrose for 20 min. at room temperature. The supernatant was saved as the "hypertonic fraction," and the cell pellet was resuspended in 10 ml of cold water. After centrifugation, the supernatant was saved as the "periplasmic fraction." The pellet was suspended in Tris-HCl buffer pH 7.3, and the cells were disrupted by sonication for two min. (1 min pulse twice) on ice. The cell lysate was centrifuged, and the supernatant was saved as the "cytoplasmic fraction."

RESULTS

Molecular cloning of the chitobiase gene. A *Vibrio parahemolyticus* Sau3A partial genomic DNA library, containing 5–8 kbp and 7–12 kbp fragments was constructed in pUC18 and screened for chitobiase activity in *E. coli* as described above. Among two thousand transformants, one *E. coli* colony (that transformed with plasmid pC120) showed chitobiase activity, as evidenced by a yellow zone on the p-nitrophenyl-β-N-acetylglucosamine-LB agar plate. The DNA from plasmid pC120 was characterized by digestion with restriction enzymes. The plasmid contained a 6.4 kb Sau3A fragment, which was cleaved by EcoRI at about 0.9 kbp from the 5' end; by SalI at about 1.4 kbp, 2.2 kbp, and 3.3 kbp from the 3' end; and by HindIII at about 3.5 kbp from the 3' end.

Intra/extracellular localization of the recombinant enzyme in *E. coli*. The culture supernatant was saved as an extracellular fraction. The cell pellet was treated with 20% sucrose in Tris-HCl pH 7.3 buffer, and the supernatant was saved as a hypertonic fraction. The periplasmic fraction was obtained by osmotic shock with cold water, and the cytoplasmic fraction was obtained by lysis of the cell pellet with sonication. As shown in Table I, the cytoplasmic fraction had 96% of the total chitobiase activity. Recall, by contrast, that the chitobiase from *V. harveyi* is transported to the outer membrane of *E. coli*, showing that these enzymes have different properties.

TABLE I

Enzymatic activities of cellular fractions of transformed *E. coli*. Units of activity: 1 µmole/min p-nitrophenol liberated from p-nitrophenyl-β-N-acetylglucosamine at pH 7.0, 25° C.

| Cell fraction | Chitobiase activity | % of total activity |
|---|---|---|
| Extracellular | <0.1 | <1 |
| Hypertonic fraction | 0.9 | 2 |
| Periplasmic fraction (Osmotic shock fraction) | 0.85 | 2 |
| Cytoplasmic fraction | 38.3 | 96 |

Purification of chitobiase from transformed *E. coli*. Cytoplasmic chitobiase was purified as described above. A summary of the purification steps and their yields is shown in Table II. Total purification following all the steps was about 110-fold, and total yield was about 23.4%.

TABLE II

Purification Yields for Recombinant Chitobiase.

| Purification step | Total activity (units) | Total protein (mg) | Specific activity (units/mg protein) |
|---|---|---|---|
| E. coli cell lysate | 3200 | 2500 | 1.24 |
| Ammonium sulfate precipitation | 2050 | 1220 | 1.68 |
| DEAE-Biogel A chromatography | 1750 | 25 | 70.0 |
| Hydroxylapatite chromatography | 1037 | 11 | 94.3 |
| Sephadex G-200 chromatography | 750 | 5.5 | 136.4 |

SDS-PAGE showed a pure homogeneous protein band at 80,000 Da. A partial N-terminal sequence of the chitobiase has been determined by gas-phase Edman technology, and is compared with a published N-terminal sequence of *Vibrio harveyi* chitobiase in the sequence listings appearing at the end of this specification. No homology is apparent. A further comparison by the inventors with other published chitobiases and β-N-acetylhexosaminidases revealed no homologies.

ENZYME CHARACTERIZATION

Km value and isoelectric point (pI). Dependence of the activity of chitobiase on substrate concentration was examined using p-nitrophenyl-β-N-acetylglucosamine as a substrate. The Km value was calculated from Lineweaver-Burk plots of the activity, and the Km for chitobiase was estimated to be 3 mM p-nitrophenyl-β-N-acetylglucosamine. A purified enzyme preparation was used for determination of the pI. Four very sharp, closely spaced bands, pI=4.975, 4.977, 5.075, 5.100, were seen on the Phast IEF 4–6.5 gel (Pharmacia, Piscataway, N.J.). All four bands contained chitobiase activity as evidenced by in situ substrate staining on the isoelectric gel with naphthol-AS-B1-β-GlcNAc (Sigma Chemical). Because the N-terminal sequence was obtained without ambiguity, these bands may be due to post-translational proteolytic cleavage near the C-terminus.

Substrate specificity: Substrates tested against the recombinant *Vibrio parahemolyticus* chitobiase are listed in the table depicted in the accompanying figures. The best substrates were p-nitrophenyl-β-N-acetylglucosamine and diacetylchitobiose. Activity towards p-nitrophenyl-β-N-acetylglucosamine was five-fold higher than that for pNP-β-GalNAc. Hydrolysis of glycosides for both these substrates allows the enzyme to be classified as an N-acetylhexosaminidase (See EC 3.2.1.52). A synthetic oligosaccharide, β-GlcNAc-(1–3)-β-Gal-(1–4)GlcNAc was also a good substrate, indicating a lack of significant discrimination between −3, and −4 linkages. The enzyme was, surprisingly, completely inactive against glycolipids containing non-reducing terminal β-GlcNAc or β-GalNAc, with or without detergents or saposins. It was inactive against all alpha-linked N-acetyl-hexosamine glycosides and p-nitrophenyl-β-N-acetylglucosamine-6-sulfate.

The table depicted in the accompanying figure gives substrate specificities of the cloned chitobiase.

Purified chitobiase from *Vibrio parahemolyticus* was incubated with the compounds listed. Activity towards each of the p-nitrophenyl derivatives was measured by the release of p-nitrophenol (O.D. 420), and activity towards other substrates was determined by TLC or HPLC.

Exochitobiase activity: The enzyme reaction products were tested by thin layer chromatography (Silica gel G, Acetonitrile:$H_2O$=3:1). Chitotetraose was used as a substrate. The products GlcNAc and chitobiose appeared earlier than chitobiose using a dilute enzyme solution at 10° C. This result implies that the enzyme acts as an exochitobiase; otherwise chitobiase should have appeared earlier.

Salt tolerance: The enzyme's activity was measured as described above. Various concentrations of NaCl (from 0M–4M) were added to the reaction buffer to examine the stability of the enzyme in salt. Enzyme activity was enhanced slightly at 0.1M NaCl. The enzyme retained 85% of its activity in pH 7.0 phosphate buffer with 1M NaCl, with 56% of the activity still remaining at 2M NaCl, 28% at 3M NaCl, and 2% at 4M NaCl.

Effect of pH: The pH was varied using the reaction conditions as otherwise described above, from pH 4 to 11. A broad pH range for enzyme activity was seen, with an optimum at 7.0, and 30% or greater relative activity over the pH range 5.0 to 9.0. Stability of the enzyme was examined by incubating with different pH buffers at 37° C. for 30 min., followed by adjusting the pH to 7.0. Treated enzyme preparations were assayed under standard conditions. The enzyme was stable to this treatment at a pH range of 6–10.5.

Thermostability: Heat tolerance was examined by maintaining the enzyme solution at various temperatures at pH 7.0, followed by mediate cooling to room temperature. The enzyme activities of the treated enzyme solutions were assayed as described above. Over 80% of enzyme activity remained after treatment at 45° C. for 60 min, while 95% of enzyme activity was lost after incubation at 50° C. for 10 min.

Definitions

As used in the claims below, the term "Chitobiase VP2" is intended to include not only exact duplicates of the enzyme expressed by the transformed *E. coli* strain whose ATCC accession number is 68920, but also any enzyme having substantially the same amino acid sequence, and substantially the same activity towards hydrolyzing chitooligomers or N-acetyl-hexosamines; including one or more of the following: p-nitrophenyl-β-N-acetylglucosamine, p-nitrophenyl-β-N-acetylgalactosamine, p-nitrophenyl-β-NN'-diacetylchitobiose, diacetylchitobiose, triacetylchitotriose, or tetraacetylchitotetraose. This definition is intended to include at least natural allelic variations in amino acid sequence.

As used in the claims below, a "substantially pure" chitobiase is one in which any contaminants which may be present: (1) are in sufficiently low concentrations as to avoid significant interference with the hydrolysis of chitooligomers; or (2) are in sufficenly low concentrations that only a single protein band is visible on SDS-PAGE. By way of example, the cloned Chitobiase VP2, purified as described above, is considered to be "substantially pure."

We claim:

1. A recombinant cloning vector adapted for transformation of a microbial host, said recombinant cloning vector comprising a vector into which a polynucleotide segment which codes for a chitobiase has been inserted; wherein the chitobiase coded by said polynucleotide segment is derived from *Vibrio parahemolyticus*; wherein the chitobiase has substantially the substrate specificity shown in the table of the figure accompanying the specification; wherein the chitobiase retains approximately 85% of its activity in pH 7.0 phosphate buffer and 1M NaCl; wherein the chitobiase retains approximately 56% of its activity in pH 7.0 phosphate buffer and 2M NaCl; and wherein the chitobiase retains approximately 28% of its activity in pH 7.0 phosphate buffer at 3M NaCl.

2. A recombinant cloning vector as recited in claim 1, wherein said recombinant cloning vector comprises plasmid pC120.

3. A transformed microorganism which includes a recombinant cloning vector as recited in claim 1.

4. A transformed microorganism as recited in claim 3, wherein said recombinant cloning vector comprises plasmid pC120.

5. A transformed microorganism as recited in claim 4, wherein said microorganism comprises a strain of *E. coli*.

6. A transformed microorganism as recited in claim 5, wherein said microorganism comprises the transformed *E. coli* strain whose ATCC accession number is 68920.

7. A process for producing Chitobiase VF2 which comprises culturing a transformed microorganism as recited in claim 3 in a suitable nutrient medium until Chitobiase VP2 is formed, and thereafter isolating the Chitobiase VP2.

8. A process as recited in claim 7, wherein said recombinant cloning vector comprises plasmid pC120.

9. A process as recited in claim 8, wherein said microorganism comprises a strain of *E. coli*.

10. A process as recited in claim 9, wherein said microorganism comprises the transformed *E. coli* strain whose ATCC accession number is 68920.

11. A synthetic gene comprising a polynucleotide segment which codes for a chitobiase; wherein the chitobiase coded by said polynucleotide segment is derived from *Vibrio parahemolyticus*; wherein the chitobiase has substantially the substrate specificity shown in the table of the figure accompanying the specification; wherein the chitobiase retains approximately 85% of its activity in pH 7.0 phosphate buffer and 1M NaCl; wherein the chitobiase retains approximately 56% of its activity in pH 7.0 phosphate buffer and 2M NaCl; and wherein the chitobiase retains approximately 28% of its activity in pH 7.0 phosphate buffer at 3M NaCl.

12. A synthetic gene as recited in claim 11, wherein said polynucleotide segment is located between two restriction endonuclease cleavage sites.

13. A vector as recited in claim 1, wherein the chitobiase coded by said polynucleotide segment has a Km of approximately 3 mM p-nitrophenyl-β-N-acetylglucosamine.

14. A vector as recited in claim 1, wherein the chitobiase coded by said polynucleotide segment has an isoelectric point between approximately pH 4.975 and approximately pH 5.100.

15. A vector as recited in claim 1, wherein the chitobiase coded by said polynucleotide segment has a molecular weight of approximately 80,000.

16. A vector as recited in claim 1, wherein the chitobiase coded by said polynucleotide segment retains approximately 30% of its activity over the pH range 5.0 to 9.0.

17. A vector as recited in claim 1, wherein the chitobiase coded by said polynucleotide segment retains approximately 80% of its activity after heating to 45° C. for sixty minutes, followed by immediate cooling to 25° C.

18. A vector as recited in claim 1, wherein the amino-terminal sequence of the chitobiase coded by said polynucleotide segment is SEQ ID NO 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Vibrio parahemolyticus ( x i ) SEQUENCE DESCRIPTION: SEQ ID NO:1:

```
Met Glu Tyr Arg Val Asp Leu Val Val Leu Ser Glu Gln Lys Gln Asn
 1               5                  10                  15

Cys Arg Phe Gly Leu Thr Phe His Asn Leu Ser Asp Gln Asp Leu His
            20                  25                  30

Asn Trp Ser Leu Ile Phe Ala Phe Asp Arg Tyr Ile Leu Pro
            35                  40                  45
```

( 2 ) INFORMATION FOR SEQ ID NO:2:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Vibrio harveyi ( x i ) SEQUENCE DESCRIPTION: SEQ ID NO:2:

```
Met Leu Lys His Ser Leu Ile Ala Ala Ser Val Ile Thr Thr Leu Ala
 1               5                  10                  15

Gly Cys Ser Ser Leu Gln Ser Ser Glu Gln Gln Val Val Asn Ser Leu
            20                  25                  30

Ala Asp Asn Leu Asp Ile Gln Tyr Glu Val Leu Thr Asn His
            35                  40                  45
```